United States Patent
Fan et al.

(10) Patent No.: US 7,125,673 B2
(45) Date of Patent: Oct. 24, 2006

(54) CPG RETRIEVAL OF DNA FROM FORMALIN-FIXED PATHOLOGY SPECIMEN FOR PROMOTER METHYLATION ANALYSIS

(76) Inventors: Chun-Yang Fan, 16 Chatel Dr., Little Rock, AR (US) 72223; Thomas Brent, 540 County Rd. 119, Walnut, MS (US) 38683

( * ) Notice: Subject to any disclaimer, the term of this patent is extended or adjusted under 35 U.S.C. 154(b) by 0 days.

(21) Appl. No.: 10/955,340

(22) Filed: Sep. 23, 2004

(65) Prior Publication Data

US 2005/0196769 A1    Sep. 8, 2005

Related U.S. Application Data

(63) Continuation-in-part of application No. PCT/US03/09106, filed on Mar. 25, 2003, now abandoned.

(60) Provisional application No. 60/367,192, filed on Mar. 25, 2002.

(51) Int. Cl.
  *C12Q 1/68*    (2006.01)
  *C12Q 19/34*   (2006.01)
  *C12Q 1/08*    (2006.01)
  *C07H 21/02*   (2006.01)

(52) U.S. Cl. .......................... 435/6; 435/91.2; 435/270; 536/23.1

(58) Field of Classification Search .................... None
  See application file for complete search history.

(56) References Cited

U.S. PATENT DOCUMENTS 5,786,146 A * 7/1998 Herman et al. ................ 435/6

FOREIGN PATENT DOCUMENTS

WO    WO 01/77377 A2 * 10/2001

OTHER PUBLICATIONS

Ai et al. Ataxia-telangiectasia-mutated (ATM) gene in head and neck squamous cell carcinoma: promoter hypermethylation with clinical correlation in 100 cases.*
Sepp et al. Rapid techniques for DNA extraction from routinely processed archival tissue for use in PCR. J Clin Pathol. Apr. 1994;47(4):318-23.*
Shi et al. Antigen retrieval immunohistochemistry: past, present, and future. J Histochem Cytochem. Mar. 1997;45(3):327-43. Review.*
Shiurba et al. Immunocytochemistry of formalin-fixed human brain tissues: microwave irradiation of free-floating sections. Brain Res Brain Res Protoc. Jan. 1998;2(2):109-19.*
Bolt et al. The ATM/p53 pathway is commonly targeted for inactivation in squamous cell carcinoma of the head and neck(SCCHN) by multiple mechanisms. Oral Oncol. Nov. 2005;41(10):1013-20. Epub Aug. 31, 2005.*

* cited by examiner

*Primary Examiner*—Jeffrey Fredman
(74) *Attorney, Agent, or Firm*—Benjamin Aaron Adler (57) ABSTRACT

The present invention provides a method, referred to as CpG retrieval, to overcome incomplete bisulfite modification of DNA recovered from formalin-fixed tissue samples. The method involves boiling deparaffinized tissue samples in citrate buffer, followed by DNA extraction for promoter methylation analysis. In general, the extracted DNA is further modified by sodium bisulfite and then subjected to a method of promoter methylation analysis. The present invention also reports that hypermethylation of ataxia-telangiectasia-mutated gene promoter is correlated with decreased overall survival in patient with head and neck squamous cell carcinoma.

3 Claims, 4 Drawing Sheets

5'-ATACTACGAGCGGTATGTGGCGGACGGCGAG-3'
(SEQ ID NO: 5)

Fig. 1A

5'-ATACTAC<u>G</u>AA<u>CG</u>ATATAT<u>A</u>AC<u>G</u>AAC<u>G</u>AC<u>GA</u>A-3'
(SEQ ID NO: 6)

Fig. 1B

5'-ATACTAC<u>G</u>AGC<u>GG</u>TAT<u>A</u>T<u>A</u>AC<u>G</u>GAC<u>GG</u>C<u>G</u>AG-3'
(SEQ ID NO: 7)

Fig. 1C

5'-ATACTAC<u>G</u>AAC<u>A</u>ATATAT<u>A</u>AC<u>G</u>AAC<u>G</u>AC<u>G</u>AA-3'
(SEQ ID NO: 8)

W: 5'-AATGTTTTGGGGCAGTGTTTTGAGCGCGGAGACCG-3'

U: 5'-AATGTTTTGGGGTAGTGTTTTGAGTGTGGAGATTG-3'

M: 5'-AATGTTTTGGGGTAGTGTTTTGAGCGCGGAGATTG-3'

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<221> NAME/KEY: primer_bind
<223> OTHER INFORMATION: F1M/R3M PCR Primers For hOGG1
      Methylation-Specific PCR

<400> SEQUENCE: 1
ggtcggagtt gtgttcgttt c                                              21

<210> SEQ ID NO 2
<211> LENGTH: 17
<212> TYPE: DNA
<213> ORGANISM: Artificial Sequence
<220> FEATURE:
<221> NAME/KEY: primer_bind
<223> OTHER INFORMATION: F1M/R3M PCR Primers For hOGG1
      Methylation-Specific PCR

<400> SEQUENCE: 2
gctcgcgcga ttaaccg                                                   17

<210> SEQ ID NO 3
<211> LENGTH: 21
<212> TYPE: DNA
<213> ORGANISM: Artificial Sequence
<220> FEATURE:
<221> NAME/KEY: primer_bind
<223> OTHER INFORMATION: F1U/R3U PCR Primers For hOGG1
      Methylation-Specific PCR

<400> SEQUENCE: 3
ggttggagtt gtgtttgttt t                                              21

<210> SEQ ID NO 4
<211> LENGTH: 21
<212> TYPE: DNA
<213> ORGANISM: Artificial Sequence
<220> FEATURE:
<221> NAME/KEY: primer_bind
<223> OTHER INFORMATION: F1U/R3U PCR Primers For hOGG1
      Methylation-Specific PCR

<400> SEQUENCE: 4
aacactcaca caattaacca a                                              21

<210> SEQ ID NO 5
<211> LENGTH: 21
<212> TYPE: DNA
<213> ORGANISM: Artificial Sequence
<220> FEATURE:
<221> NAME/KEY: primer_bind
<223> OTHER INFORMATION: F3M/R3M PCR Primers For hOGG1
      Methylation-Specific PCR

<400> SEQUENCE: 5
gttcggggga gaacggtttt c                                              21

<210> SEQ ID NO 6
<211> LENGTH: 17
<212> TYPE: DNA
<213> ORGANISM: Artificial Sequence

```
<220> FEATURE:
<221> NAME/KEY: primer_bind
<223> OTHER INFORMATION: F3M/R3M PCR Primers For hOGG1
      Methylation-Specific PCR

<400> SEQUENCE: 6
gctcgcgcga ttaaccg                                                    17

<210> SEQ ID NO 7
<211> LENGTH: 21
<212> TYPE: DNA
<213> ORGANISM: Artificial Sequence
<220> FEATURE:
<221> NAME/KEY: primer_bind
<223> OTHER INFORMATION: F3U/R3U PCR Primers For hOGG1
      Methylation-Specific PCR

<400> SEQUENCE: 7
gtttggggga gaatggtttt t                                               21

<210> SEQ ID NO 8
<211> LENGTH: 21
<212> TYPE: DNA
<213> ORGANISM: Artificial Sequence
<220> FEATURE:
<221> NAME/KEY: primer_bind
<223> OTHER INFORMATION: F3U/R3U PCR Primers For hOGG1
      Methylation-Specific PCR

<400> SEQUENCE: 8
aacactcaca caattaacca a                                               21

<210> SEQ ID NO 9
<211> LENGTH: 21
<212> TYPE: DNA
<213> ORGANISM: Artificial Sequence
<220> FEATURE:
<221> NAME/KEY: primer_bind
<223> OTHER INFORMATION: F4M/R3M PCR Primers For hOGG1
      Methylation-Specific PCR

<400> SEQUENCE: 9
cggatagttt tgaggaatcg c                                               21

<210> SEQ ID NO 10
<211> LENGTH: 17
<212> TYPE: DNA
<213> ORGANISM: Artificial Sequence
<220> FEATURE:
<221> NAME/KEY: primer_bind
<223> OTHER INFORMATION: F4M/R3M PCR Primers For hOGG1
      Methylation-Specific PCR

<400> SEQUENCE: 10
gctcgcgcga ttaaccg                                                    17

<210> SEQ ID NO 11
<211> LENGTH: 21
<212> TYPE: DNA
<213> ORGANISM: Artificial Sequence
<220> FEATURE:
<221> NAME/KEY: primer_bind
<223> OTHER INFORMATION: F4U/R3U PCR Primers For hOGG1
      Methylation-Specific PCR

<400> SEQUENCE: 11
tggatagttt tgaggaattg t                                               21
```

```
<210> SEQ ID NO 12
<211> LENGTH: 21
<212> TYPE: DNA
<213> ORGANISM: Artificial Sequence
<220> FEATURE:
<221> NAME/KEY: primer_bind
<223> OTHER INFORMATION: F4U/R3U PCR Primers For hOGG1
      Methylation-Specific PCR

<400> SEQUENCE: 12
aacactcaca caattaacca a                                              21

<210> SEQ ID NO 13
<211> LENGTH: 26
<212> TYPE: DNA
<213> ORGANISM: Artificial Sequence
<220> FEATURE:
<221> NAME/KEY: primer_bind
<223> OTHER INFORMATION: F9MB/R5M PCR Primers For hOGG1
      Methylation-Specific PCR

<400> SEQUENCE: 13
ggtagagagt ttagtgtcgg ttaatc                                         26

<210> SEQ ID NO 14
<211> LENGTH: 21
<212> TYPE: DNA
<213> ORGANISM: Artificial Sequence
<220> FEATURE:
<221> NAME/KEY: primer_bind
<223> OTHER INFORMATION: F9MB/R5M PCR Primers For hOGG1
      Methylation-Specific PCR

<400> SEQUENCE: 14
gcttcgtacc ccaattctcc g                                              21

<210> SEQ ID NO 15
<211> LENGTH: 26
<212> TYPE: DNA
<213> ORGANISM: Artificial Sequence
<220> FEATURE:
<221> NAME/KEY: primer_bind
<223> OTHER INFORMATION: F9U/R5U PCR Primers For hOGG1
      Methylation-Specific PCR

<400> SEQUENCE: 15
gtttagtgtt ggttaattgt gtgagt                                         26

<210> SEQ ID NO 16
<211> LENGTH: 24
<212> TYPE: DNA
<213> ORGANISM: Artificial Sequence
<220> FEATURE:
<221> NAME/KEY: primer_bind
<223> OTHER INFORMATION: F9U/R5U PCR Primers For hOGG1
      Methylation-Specific PCR

<400> SEQUENCE: 16
cccacttcat accccaattc tcca                                           24

<210> SEQ ID NO 17
<211> LENGTH: 22
<212> TYPE: DNA
<213> ORGANISM: Artificial Sequence
<220> FEATURE:
<221> NAME/KEY: primer_bind
<223> OTHER INFORMATION: F8MB/R6M PCR Primers For hOGG1
      Methylation-Specific PCR
```

```
<400> SEQUENCE: 17
cgaagcgggg ttttgatgat tc                                         22

<210> SEQ ID NO 18
<211> LENGTH: 21
<212> TYPE: DNA
<213> ORGANISM: Artificial Sequence
<220> FEATURE:
<221> NAME/KEY: primer_bind
<223> OTHER INFORMATION: F8MB/R6M PCR Primers For hOGG1
      Methylation-Specific PCR

<400> SEQUENCE: 18
acgcctaaac aaaaacgcgc g                                          21

<210> SEQ ID NO 19
<211> LENGTH: 24
<212> TYPE: DNA
<213> ORGANISM: Artificial Sequence
<220> FEATURE:
<221> NAME/KEY: primer_bind
<223> OTHER INFORMATION: F8U/R6UB PCR Primers For hOGG1
      Methylation-Specific PCR

<400> SEQUENCE: 19
agttggagaa ttggggtatg aagt                                       24

<210> SEQ ID NO 20
<211> LENGTH: 26
<212> TYPE: DNA
<213> ORGANISM: Artificial Sequence
<220> FEATURE:
<221> NAME/KEY: primer_bind
<223> OTHER INFORMATION: F8U/R6UB PCR Primers For hOGG1
      Methylation-Specific PCR

<400> SEQUENCE: 20
cccatacacc taaacaaaaa cacaca                                     26

<210> SEQ ID NO 21
<211> LENGTH: 29
<212> TYPE: DNA
<213> ORGANISM: Artificial Sequence
<220> FEATURE:
<221> NAME/KEY: primer_bind
<223> OTHER INFORMATION: sense primers for unmethylated hMLH1 promoter

<400> SEQUENCE: 21
ttttgatgta gatgttttat tagggttgt                                  29

<210> SEQ ID NO 22
<211> LENGTH: 24
<212> TYPE: DNA
<213> ORGANISM: Artificial Sequence
<220> FEATURE:
<221> NAME/KEY: primer_bind
<223> OTHER INFORMATION: antisense primers for unmethylated hMLH1 promoter

<400> SEQUENCE: 22
accacctcat cataactacc caca                                       24

<210> SEQ ID NO 23
<211> LENGTH: 24
<212> TYPE: DNA
<213> ORGANISM: Artificial Sequence
<220> FEATURE:
```

```
<221> NAME/KEY: primer_bind
<223> OTHER INFORMATION: sense primers for methylated hMLH1 promoter

<400> SEQUENCE: 23
acgtagacgt tttattaggg tcgc                                          24

<210> SEQ ID NO 24
<211> LENGTH: 20
<212> TYPE: DNA
<213> ORGANISM: Artificial Sequence
<220> FEATURE:
<221> NAME/KEY: primer_bind
<223> OTHER INFORMATION: antisense primers for methylated hMLH1 promoter

<400> SEQUENCE: 24
cctcatcgta actacccgcg                                               20

<210> SEQ ID NO 25
<211> LENGTH: 24
<212> TYPE: DNA
<213> ORGANISM: Artificial Sequence
<220> FEATURE:
<221> NAME/KEY: primer_bind
<223> OTHER INFORMATION: sense primers for unmethylated ATM promoter

<400> SEQUENCE: 25
gttttggagt ttgagttgaa gggt                                          24

<210> SEQ ID NO 26
<211> LENGTH: 22
<212> TYPE: DNA
<213> ORGANISM: Artificial Sequence
<220> FEATURE:
<221> NAME/KEY: primer_bind
<223> OTHER INFORMATION: antisense primers for unmethylated ATM promoter

<400> SEQUENCE: 26
aactacctac tcccacttcc aa                                            22

<210> SEQ ID NO 27
<211> LENGTH: 19
<212> TYPE: DNA
<213> ORGANISM: Artificial Sequence
<220> FEATURE:
<221> NAME/KEY: primer_bind
<223> OTHER INFORMATION: sense primers for methylated ATM promoter

<400> SEQUENCE: 27
ggagttcgag tcgaagggc                                                19

<210> SEQ ID NO 28
<211> LENGTH: 20
<212> TYPE: DNA
<213> ORGANISM: Artificial Sequence
<220> FEATURE:
<221> NAME/KEY: primer_bind
<223> OTHER INFORMATION: antisense primers for methylated ATM promoter

<400> SEQUENCE: 28
ctacctactc ccgcttccga                                               20
```

CPG RETRIEVAL OF DNA FROM FORMALIN-FIXED PATHOLOGY SPECIMEN FOR PROMOTER METHYLATION ANALYSIS

CROSS-REFERENCE TO RELATED APPLICATION

This is a continuation-in-part application of International Application PCT/US03/09106, with an international filing date of Mar. 25, 2003, now abandoned, which claims benefit of provisional application U.S. Ser. No. 60/387,192, filed Mar. 25, 2002, now abandoned.

BACKGROUND OF THE INVENTION

1. Field of the Invention

The present invention relates generally to the study of promoter hypermethylation. More specifically, the present invention provides a method to overcome incomplete bisulfite modification of DNA recovered from formalin-fixed tissue samples.

2. Description of the Related Art

In higher order eukaryotic organisms, DNA is methylated only at cytosines located 5' to guanosine in the CpG dinucleotide. CpG rich areas (CpG islands) comprise about 1% of vertebrate genomes and account for about 15% of the total number of CpG dinucleotides. CpG islands are typically between 0.2 to about 1 kb in length and are located upstream of many housekeeping and tissue-specific genes, but may also extend into gene coding regions.

Methylation of cytosine residues within CpG islands plays important role in gene inactivation, cell differentiation, tumorigenesis, X-chromosome inactivation, and genomic imprinting. Extensive methylation of CpG islands has been associated with transcriptional inactivation of selected imprinted genes and genes on the inactive X chromosome of females. CpG islands of constitutively-expressed housekeeping genes are normally unmethylated in the germline and in somatic tissues. Tissue-specific genes are usually unmethylated in the receptive target organs but are methylated in the germline and in non-expressing adult tissues.

Aberrant methylation of normally unmethylated CpG islands has been described as a frequent event in immortalized and transformed cells and has been frequently associated with transcriptional inactivation of tumor suppressor genes in human cancers. Increased methylation of CpG islands associated with tumor suppressor genes may lead to progressive reduction of normal gene expression resulting in the selection of a population of cells having a selective growth advantage (i.e., a malignancy). It is considered that an altered DNA methylation pattern, particularly methylation of cytosine residues, causes genome instability and is mutagenic.

In recent years, emerging evidence indicates that epigenetic alterations associated with promoter hypermethylation is one of the most common molecular events in human neoplasia and this epigenetic change works closely with genetic alterations (coding-region mutation) in human carcinogenesis. Loss of gene function due to promoter hypermethylation has characteristics that mimic the loss of tumor-suppressor gene function due to genetic alterations. Hypermethylation of one allele is frequently accompanied by deletion of the opposite allele, resulting in loss of heterozygosity of the gene. Gene inactivation associated with promoter hypermethylation is fully heritable and loss of gene function due to promoter hypermethylation leads to selective growth advantage in a manner identical to loss of tumor-suppressor gene function.

A number of housekeeping genes are inactivated primarily via promoter hypermethylation in human cancers. A housekeeping gene is a gene of general importance and expresses in a wide variety of organs and tissues. Characteristically, a housekeeping gene contains CpG islands and is devoid of TATA or CAAT boxes in its promoter. The expression of these CpG island-containing housekeeping genes is regulated frequently via promoter CpG island methylation. Genes involved in DNA repair are functionally very important as reflected by their expression in a wide variety of tissues. DNA repair genes, such as hOGG1, hMLH1, MGMT, a gene specific for repair of $O^6$-methylguanine, and NTH1, a gene specific for repair of thymine glycol, all contain CpG islands in their promoter, indicating that these important DNA repair genes are subjected to regulation by promoter methylation.

Methylation-specific PCR (MSP) has recently been developed and used to analyze promoter methylation status of various genes (Herman et al., 1996). One fundamental element of the methylation-specific PCR is to modify DNA using sodium bisulfite before the PCR reaction. In this process, all cytosines not in the CpG sequence (non-CpG cytosines) will be converted to thymine because they are all inevitably free of methylation. On the other hand, cytosines in the CpG sequence (CpG cytosines) will remain as cytosine if the C is methylated but will be converted to thymine if the C is not methylated. This method is considered to be the most sensitive and specific method for promoter methylation determination.

Currently, the methylation-specific PCR method is primarily used with DNA samples extracted from fresh tissues or cells in culture and is only applied sporadically to formalin-fixed, paraffin-embedded tissues. DNA extracted from formalin-fixed tissues is of poor quality and may still contain formalin-induced DNA/DNA or DNA/protein crosslinks that survive the extraction processes. Thus, the prior art is deficient in a method of analyzing promoter methylation in DNA isolated from formalin-fixed, paraffin-embedded tissues. The present invention fulfills this long-standing need and desire in the art.

SUMMARY OF THE INVENTION

The present invention provides a method of preparing DNA from paraffin-embedded, formalin-fixed tissue samples for promoter methylation analysis. The formalin-fixed tissue samples are usually obtained from cancer patients. The method involves boiling deparaffinized tissue samples in citrate buffer, followed by DNA extraction for promoter methylation analysis. In one embodiment, the tissue samples are boiled in 1× citrate buffer for 30 minutes. In general, the extracted DNA is further modified by sodium bisulfite and then subjected to a method of promoter methylation analysis that involves the use of bisulfite-modified DNA. One example of such a method of promoter methylation analysis is methylation-specific PCR.

The present invention also provides a method of predicting overall patient survival for patient with head and neck squamous cell carcinoma. The method involves a step of determining promoter methylation status of ataxia-telangiectasia-mutated (ATM) gene, wherein hypermethylation of the ATM gene promoter indicates the patient would have decreased overall survival. In one embodiment, promoter methylation status is determined by methylation-specific PCR. Preferably, the methylation-specific PCR utilizes pairs of primers selected from SEQ ID NOs: 25–28.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A represents a wild-type sequence and FIG. 1B is an example of a methylated DNA sequence being modified by bisulfite treatment. Single underlined are non-CpG cytosines that are converted to thymines. In an antisense sequence such as this, A is present instead of T. Double underlined are methylated cytosines at CpG sequence that remain unchanged (G is present in the place of C).

FIG. 1C is a sequence from DNA extracted from formalin-fixed tumor tissue before CpG retrieval. Most of the non-CpG cytosines are not converted to thymines and remain as cytosines following bisulfite treatment (bolded G). Only 3 out of 8 non-CpG cytosines are converted to thymines (single underlined A). Because of incomplete modification of non-CpG cytosines, the methylation status at the CpG cytosines could not be accurately assessed (bolded G, double-underlined).

FIG. 1D is a sequence derived from the same DNA sample as that for FIG. 1C but after CpG retrieval. Here, all non-CpG cytosines are successfully converted to thymines (single-underlined A). Most CpG cytosines are methylated, which are viewed as G (double-underlined) in an antisense sequence except for one (A, bolded and single-underlined) which is free of methylation and thus is successfully converted.

FIG. 2A is a schematic diagram of the ataxia-telangiectasia-mutated (ATM) proximal promoter region. The location of the methylation specific PCR (MSP) primer sets relative to the ATM and NPAT genes are given. Cross-hatches, the location of CpG dinucleotides within this intergenic region; U, unmethylated-specific; M, methylated-specific; F, forward primer; R, reverse primer.

FIG. 3A shows bisulfite-modified DNA harvested from HNSCC tumors designated case 1 (Lanes 1 and 2), case 10 (Lanes 3 and 4), case 23 (Lanes 5 and 6), case 26 (Lanes 7 and 8), and case 78 (Lanes 9 and 10) were subjected to methylation specific PCR (MSP) using unmethylated (U) or methylated-specific (M) MSP primer sets.

FIG. 3B shows DNA sequencing results obtained from cloned methylation-specific amplicon obtained from a head and neck squamous cell carcinoma tumor (case 26 in FIG. 3A). W, wildtype sequence of this region of the ATM promoter; U, predicted sequence after bisulfite modification if this sequence is unmethylated [all cytosines (Cs) are converted to thymines (Ts) after bisulfite modification (single underline)]; M, sequence obtained from the cloned methylation-specific amplicon. Also shown is sequencing chromatogram from this clone. Two of the three C residues within CpG dinucleotides (double underline) are not converted to T residues after bisulfite modification, indicating their positive methylation status. The last CpG cytosine is not methylated in this particular clone and, thus, is converted to thymine (T) after bisulfite modification (double underline).

FIG. 3C shows bisulfite-modified DNA harvested from five non-neoplastic tonsillectomy specimens designated case 1 (Lanes 1 and 2), case 2 (Lanes 3 and 4), case 3 (Lanes 5 and 6), case 4 (Lanes 7 and 8) and case 5 (Lanes 9 and 10) were subjected to methylation specific PCR (MSP) using unmethylated (U) or methylated-specific (M) MSP primer sets.

FIG. 4A: overall survival was calculated based on total death of all causes according to entire patient population. FIG. 4B: survival was calculated based on total death of all causes in patients diagnosed with T1 tumors. FIG. 4C: survival was calculated based on total death of all causes in patients diagnosed with N0 tumors. Patients were grouped by presence of ATM promoter methylation (solid line, ATM MSP+) and absence of ATM promoter methylation (broken line, ATM MSP−).

DETAILED DESCRIPTION OF THE INVENTION

Methods for DNA methylation pattern determinations at specific loci usually rely on techniques that alter the genomic DNA in a methylation-dependent manner. Changes in methylation patterns at specific CpG sites can be monitored by digestion of genomic DNA with methylation-sensitive restriction enzymes followed by Southern analysis of the regions of interest (digestion-Southern method). The digestion-Southern method is a straightforward method but it requires a large amount of high molecular weight DNA. Another method of analyzing changes in methylation patterns involves a PCR-based process that involves digestion of genomic DNA with methylation-sensitive restriction enzymes prior to PCR amplification.

The other technique that has received recent widespread use is the treatment of genomic DNA with sodium bisulfite. Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. Currently, all bisulfite treatment-based methods are followed by a PCR reaction to analyze specific loci within the genome.

There are two principally different ways in which the sequence difference generated by the sodium bisulfite treatment can be revealed. The first is to design PCR primers that uniquely anneal with either methylated or unmethylated converted DNA. This technique is referred to as "methylation specific PCR" or "MSP". The method used by all other bisulfite-based techniques (such as bisulfite genomic sequencing, COBRA and Ms-SNuPE) is to amplify the bisulfite-converted DNA using primers that anneal at locations that lack CpG dinucleotides in the original genomic sequence. In this way, the PCR primers can amplify the sequence in between the two primers, regardless of the DNA methylation status of that sequence in the original genomic DNA. This results in a pool of different PCR products, all with the same length and differing in their sequence only at the sites of potential DNA methylation at CpGs located in between the two primers. The difference between these methods of processing the bisulfite-converted sequence is that in methylation specific PCR, the methylation information is derived from the occurrence or lack of occurrence of a PCR product, whereas in the other techniques a mixture of products is always generated that is subsequently analyzed to yield quantitative information on the relative occurrence of the different methylation states.

The method of methylation-specific PCR is considered to be the most sensitive and specific method for promoter methylation determination. Currently, methylation-specific PCR is primarily used with DNA samples extracted from fresh tissues or cells in culture. The method cannot be successfully applied to formalin-fixed, paraffin-embedded tissues samples because DNA extracted from formalin-fixed tissues may still contain formalin-induced DNA/DNA or DNA/protein crosslinks that hinder chemical modification of DNA by sodium bisulfite prior to methylation-specific PCR. Incomplete bisulfite modification of non-CpG cytosines would result in inaccurate analysis of promoter methylation by methylation-specific PCR.

The present invention provides a method to overcome incomplete bisulfite modification of DNA recovered from formalin-fixed tissue samples. The method disclosed herein, referred to as CpG retrieval, involves boiling deparaffinized tissue samples in citrate buffer before bisulfite modification and methylation-specific PCR. CpG retrieval greatly improves the efficiency of bisulfite modification of DNA from formalin-fixed tissues samples. It is simple and fast. Currently, there is no existing method of this kind used in conjunction with methylation-specific PCR on formalin-fixed tissue samples. CpG retrieval is similar to antigen retrieval procedure applied in immunohistochemical staining in that both methods use heat treatment of tissues in citrate buffer. CpG retrieval, however, differs from antigen retrieval in that CpG retrieval recovers the cytosines that are otherwise unmodifiable by sodium bisulfite, as opposed to antigen retrieval that retrieves protein antigen that are otherwise undetectable by antibody due to formalin-induced cross-links.

Thus, the present invention is drawn to a method of preparing DNA from paraffin-embedded, formalin-fixed tissue samples for promoter methylation analysis. The method involves boiling deparaffinized tissue samples in citrate buffer, followed by DNA extraction for promoter methylation analysis. In general, the extracted DNA is further modified by sodium bisulfite and then subjected to a method of promoter methylation analysis that involves the use of bisulfite-modified DNA. One example of such a method of promoter methylation analysis is methylation-specific PCR. The formalin-fixed tissue samples are usually obtained from cancer patients. In one embodiment of present invention, the tissue samples are boiled in 1× citrate buffer for 30 minutes.

One of ordinary skill in the art would recognize that the present invention is not limited to DNA treatment prior to sodium bisulfite modification in methylation-specific PCR. The present invention is equally applicable to other methods of bisulfite-based promoter methylation analysis. As used herein, "bisulfite-based promoter methylation analysis" refers to methods of analyzing promoter methylation that involve DNA modification by sodium bisulfite.

In addition to those discussed above, other bisulfite-based methods known in the art include a simplified genomic sequencing technique for the analysis of DNA methylation patterns and 5-methylcytosine distribution (Frommer et al., 1992), restriction enzyme digestion of PCR products amplified from bisulfite-converted DNA (Sadri and Hornsby, 1996; Xiong and Laird, 1997), and an improved high-throughput and quantitative process for determining methylation patterns disclosed in U.S. Pat. No. 6,331,393.

The CpG retrieval method disclosed herein can improve the efficiency of complete bisulfite modification of DNA from formalin-fixed tissue samples up to about 80%. Some non-CpG cytosines in the formalin-fixed samples remain non-converted after bisulfite treatment. Thus, the CpG retrieval method described herein can be further modified to achieve bisulfite modification efficiency that is very similar to that obtained with DNA isolated from fresh tissue or cells. Experiments to demonstrate the effect of formalin fixation (the length of time during which the tissues are fixed) of human tissues on the efficiency of bisulfite modification are examined. In addition, the effects of Citrate buffer concentration and treatment time on the efficiency of CpG Retrieval on improving the bisulfite-mediated DNA modification on formalin fixed tissues is also examined.

The present invention also provides a method of predicting overall patient survival for patient with head and neck squamous cell carcinoma. The method involves extracting genomic DNA from patient tissue samples and determining promoter methylation status of ataxia-telangiectasia-mutated (ATM) gene. Hypermethylation of the ATM gene promoter indicates the patient would have decreased overall survival. In one embodiment, promoter methylation status is determined by methylation-specific PCR. Preferably, the methylation-specific PCR utilizes pairs of primers selected from SEQ ID NOs: 25–28.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Promoter Methylation Analysis

Using the surgical pathology files of Arkansas Central Healthcare System, Little Rock (November 1990–November 1999) and of the University Hospital of Arkansas, University of Arkansas for Medical Sciences, Little Rock (July 1997–November 1999), 413 cases of head and neck squamous cell carcinoma (HNSCC) were identified and retrieved with available microscopic slides and paraffin-embedded tissue blocks. Each case was individually examined microscopically. A tissue section was only considered satisfactory for the study if it contained normal mesenchymal tissues (skeletal muscle and/or salivary glands) and two or more of the following components: normal squamous mucosa, dysplasia, carcinoma in situ, and invasive cancer. Small biopsy specimens consisting exclusively of tumor were excluded from the study. Four-micron thick recut unstained histologic sections were obtained from each selected block for morphologic examination by hematoxylin and eosin staining. For promoter methylation analysis, five 5-micron thick sections were cut into eppendorf tube used for DNA extraction and bisulfite modification.

DNA samples were collected using the EX-WAX™ DNA Extraction Kit (Intergen Co., New York; Cat# S4530). Five 5-μm thick sections from each tissue block were cut, deparaffinized with xylene for three times in eppendorf tubes, clear off xylene by washing in 75% ethanol for three times and air-dry. Next, the deparaffinized tissues were boiled in 1× citrate buffer (Citrate buffer solution, pH 6.0; Zymed laboratories Inc., San Francisco) for 30 minutes before DNA extraction. This necessary step maximizes the efficiency of conversion of non-CpG cytosines to thymines by bisulfite treatment and is referred to as "CpG retrieval". DNA from fresh tonsillectomy specimen of a patient without history of head and neck squamous cell carcinoma was used as a negative control with methylated-specific primers but as a positive control with unmethylated-specific primers. CpGenome™ universal methylated DNA (human male genomic DNA; Intergen Co., New York; Cat# S7821) was used as a positive control with methylated-specific primers but as a negative control with unmethylated-specific primers.

Prior to methylation-specific PCR, DNA from patient samples, negative and positive controls were subjected to bisulfite modification using CpGenome™ DNA modification Kit (Intergen Co., New York; Cat# S7820). Amplification of promoter regions of the hOGG1 and hMLH1 gene by methylation-specific PCR was carried out in a Touchgene Gradient Thermal Cycler (Techne Inc., Princeton, N.J., Cat#2048400). The 50-μl PCR reaction mixture contained 2 μl of bisulfite-treated genomic DNA, dNTPs (each at 200 μM), primers (50 pmol each per reaction), 2.5 mM MgCl$_2$, and 1.25 units Hotstar Taq (Qiagen; Cat# 203205) in 1×PCR buffer. All reagents were supplied with the Qiagen Hotstar Taq Kit (Qiagen, Valencia, Calif., Cat# 203205) except for the dNTP mix (Roche Mol. Biochem., Cat# 1814362).

The PCR conditions were as follows: initial degeneration and hot start at 95° C. for 15 minutes; then 40 cycles consisting of 30 seconds at 95° C., 30 seconds at the annealing temperature specific for each pair of primers, and 1 minute at 72° C., followed by a final 5-min extension at 72° C. Positive and negative control DNA samples and control without DNA were performed for methylation-specific PCR.

For the hOGG1 gene promoter methylation analysis, 5 sets of paired methylated/unmethylated-specific primers were used. The primer sequences and annealing temperatures are listed in Table 1. The 5 overlapping primer sets cover the hOGG1 gene promoter region from −396 to +339 (735 bp) within a CpG island in relation to the transcription start site. For the hMLH1 gene, primer sequences of hMLH1 for the unmethylated reaction are 5'-TTT TGA TGT AGA TGT TTT ATT AGG GTT GT-3' (sense) (SEQ ID NO:21) and 5'-ACC ACC TCA TCA TAA CTA CCC ACA-3' (antisense) (SEQ ID NO:22), and for the methylated reaction, they are 5'-ACG TAG ACG TTT TAT TAG GGT CGC-3' (sense) (SEQ ID NO:23) and 5'-CCT CAT CGT AAC TAC CCG CG-3' (antisense) (SEQ ID NO:24) as described previously (Fleisher et al., 1999, 2000). All primers are purchased from Operon Technologies Inc.

Amplified PCR products were ligated into pCR4-TOPO vector and transformed into *Esterichia Coli* using TOPO TA cloning Kit for sequencing (Invitrogen Life Technologies, Carlsbad, Calif.; Cat# K4575). Plasmid DNA isolated from *E. Coli* colonies was sequenced using an Applied Biosystems (Foster City, Calif.), Model 377 DNA Sequencer. Templates were at 100 ng/ml. T3 universal primer was used in all reactions at 1.6 μM. The chemistry was Big Dye Terminator and used the Applied Biosystems Dye Terminator Kit version 2.0 according to manufacturer's instructions.

TABLE 1

PCR Primers used For hOGG1 Methylation-Specific PCR

| Primer sets[D] | Primer 5' → 3' (sense)[A]<br>Primer 5' → 3' (antisense)[A] | (bp) | Size<br>Tm[B] | Ann.<br>Posi-<br>tion[C] | Genomic |
|---|---|---|---|---|---|
| F1M/R3M | GGT<u>C</u>GGAGTTGTGTT<u>C</u>GTTT<u>C</u><br>GCTC<u>G</u>C<u>G</u>CGATTAACC<u>G</u> | (SEQ ID NO:1)<br>(SEQ ID NO:2) | 267 | 62 | −396/−129 |
| F1U/R3U | GGT<u>T</u>GGAGTTGTGTT<u>T</u>GTTT<u>T</u><br>AAC<u>A</u>CTC<u>A</u>C<u>A</u>CAATTAACC<u>A</u><u>A</u> | (SEQ ID NO:3)<br>(SEQ ID NO:4) | 270 | 56 | −396/−132 |
| F3M/R3M | GTT<u>C</u>GGGGAGAA<u>C</u>GGTTTT<u>C</u><br>GCTC<u>G</u>C<u>G</u>CGATTAACC<u>G</u> | (SEQ ID NO:5)<br>(SEQ ID NO:6) | 180 | 62 | −309/−129 |
| F3U/R3U | GTT<u>T</u>GGGGAGAA<u>T</u>GGTTTT<u>T</u><br>AAC<u>A</u>CTC<u>A</u>C<u>A</u>CAATTAACC<u>A</u><u>A</u> | (SEQ ID NO:7)<br>(SEQ ID NO:8) | 183 | 56 | −309/−132 |
| F4M/R3M | <u>C</u>GGATAGTTTTGAGGAAT<u>C</u>G<u>C</u><br>GCTC<u>G</u>C<u>G</u>CGATTAACC<u>G</u> | (SEQ ID NO:9)<br>(SEQ ID NO:10) | 124 | 62 | −253/−129 |
| F4U/R3U | <u>T</u>GGATAGTTTTGAGGAATT<u>G</u><u>T</u><br>AAC<u>A</u>CTC<u>A</u>C<u>A</u>CAATTAACC<u>A</u><u>A</u> | (SEQ ID NO:11)<br>(SEQ ID NO:12) | 127 | 56 | −253/−132 |
| F9MB/R5M | GGTAGAGAGTTTAGTGT<u>C</u>GGTTAAT<u>C</u><br>GCTTC<u>G</u>TACCCCAATTCTCC<u>G</u> | (SEQ ID NO:13)<br>(SEQ ID NO:14) | 279 | 63 | −163/+116 |

TABLE 1-continued

PCR Primers used For hOGG1 Methylation-Specific PCR

| Primer sets[D] | Primer 5' → 3' (sense)[A]<br>Primer 5' → 3' (antisense)[A] | (bp) | Size<br>Tm[B] | Ann.<br>Posi-<br>tion[C] | Genomic |
|---|---|---|---|---|---|
| F9U/R5U | GTTTAGTGTTGGTTAATTGTGTGAGT<br>CCCACTTCATACCCCAATTCTCCA | (SEQ ID NO:15)<br>(SEQ ID NO:16) | 274 | 62 | −145/+118 |
| F8MB/R6M | CGAAGCGGGGTTTTGATGATTC<br>ACGCCTAAACAAAAACGCGCG | (SEQ ID NO:17)<br>(SEQ ID NO:18) | 229 | 63 | +111/+339 |
| F8U/R6UB | AGTTGGAGAATTGGGGTATGAAGT<br>CCCATACACCTAAACAAAAACACACA | (SEQ ID NO:19)<br>(SEQ ID NO:20) | 252 | 62 | +93/+344 |

[A]Sequence differences between modified and unmodified DNA are in bold-face type and differences between methylated/modified and unmethylated/modified are underlined.
[B]Annealing temperature.
[C]Genomic position is the locations of forward and reverse primers in relation to the transcriptional start site.
[D]M designates methylated-specific primers and U designates unmethylated-specific primers.

EXAMPLE 2

CpG Retrieval of DNA from Formalin-Fixed Samples

Methylation-specific PCR (MSP) was developed to analyze promoter methylation status of various genes. DNA is modified prior to methylation-specific PCR by sodium bisulfite so that all cytosines that are free of methylation are converted to thymine. Only those cytosines in the CpG sequence (CpG cytosines) that are methylated will remain as cytosines.

It was observed that when methylation-specific PCR was applied to paraffin-embedded, formalin-fixed pathology specimen, the chemical modification of DNA by sodium bisulfite was incomplete. Up to 80% of cytosines that are not in the CpG sequence (non-CpG cytosines) could not be converted to thymine after bisulfite treatment. The number of the non-CpG cytosines resistant to bisulfite modification varied among different samples and this was probably due to variations in the duration of formalin fixation. Such insufficient modification by sodium bisulfite was seen in both hOGG1 and hMLH1 genes.

In contrast, the bisulfite modification of the DNA samples from fresh tissue was highly sufficient and complete. Incomplete bisulfite modification of non-CpG cytosines would hinder accurate interpretation of promoter methylation by methylation-specific PCR.

It was hypothesized that the incomplete bisulfite modification was due to formalin-induced DNA/protein or DNA/DNA cross-links and that such cross-links would prevent cytosines from being chemically modified by sodium bisulfite. Based on the above hypothesis, various methods (see Table 2) were tried in an attempt to break these cross-links: A) boil deparaffinized tissue sections in 1× Citrate buffer (Zymed Lab. Inc., San Francisco, Calif.) for 30 minutes; B) boil deparaffinized tissue sections in 0.2 M NaCl$_2$ solution for 30 minutes; C) incubate isolated DNA in 0.2 M NaCl$_2$ solution at 65° C. for 4 hours; D) incubate deparaffinized tissue sections in 0.2 M NaCl$_2$ solution at 65° C. for 4 hours; E) no treatment. Methods B to D are similar to that used in chromatin immunoprecipitation (CHIP) to reverse formalin-induced cross-links.

Following treatments A through E, DNA samples were extracted and modified with sodium bisulfite. The samples were then subjected to methylation-specific PCR and direct DNA sequencing. As summarized in the Table 2, 4 out of 5 DNA samples (80%) displayed 100% conversion rate (i.e. all non-CpG cytosines were successfully converted to thymines) with method A while only 2 out of 5 samples (40%) had conversion rate of 100% with methods B, C, D and E. Extremely low conversion rate (i.e. less than 20% of non-CpG cytosines were converted to thymines) was seen in 20 to 40% samples using methods B to E but not with method A. Since method A is similar to antigen retrieval procedure applied in immunohistochemical staining in that both methods use heat treatment of tissues in citrate buffer, method A is referred to as "CpG retrieval".

TABLE 2

Effects of Citrate Buffer or 0.2 M NaCl$_2$ Solution On Conversion of Non-CpG Cytosines To Thymines Following Bisulfite Treatment of DNA Extracted From Formalin-Fixed HNSCC Tissues

| | Methods Investigated | | | | |
|---|---|---|---|---|---|
| Conversion rate* | A | B | C | D | E |
| 100% | 4 | 2 | 2 | 2 | 2 |
| 50% to 100% | 1 | 1 | 2 | 1 | 1 |
| Less than 20% | 0 | 2 | 1 | 2 | 2 |
| Total Sample# | 5 | 5 | 5 | 5 | 5 |

*percentage of non-CpG cytosine being converted to thymine following bisulfite treatment.

A representative DNA sequence chromatogram is displayed in FIG. 1, illustrating the effect CpG retrieval on sodium bisulfite-mediated DNA modification. FIGS. 1A–1D are antisense sequences of part of the hMLH1 gene promoter. FIG. 1A represents a wild-type sequence and FIG. 1B is an example of a methylated DNA sequence being modified by bisulfite treatment. Single underlined are non-CpG cytosines that are converted to thymines. In an antisense sequence such as this, A is present instead of T. Double underlined are methylated cytosines at CpG sequence that remain unchanged (G is present in the place of C). FIG. 1C is a sequence from DNA extracted from formalin-fixed tumor tissue before CpG retrieval. Most of the non-CpG cytosines are not converted to thymines and remain as cytosines following bisulfite treatment (bolded G). Only 3 out of 8 non-CpG cytosines are converted to thymines (single underlined A). Because of incomplete modification of non-CpG cytosines, the methylation status at the CpG cytosines could not be accurately assessed (bolded G, double-underlined).

Figure 1A:
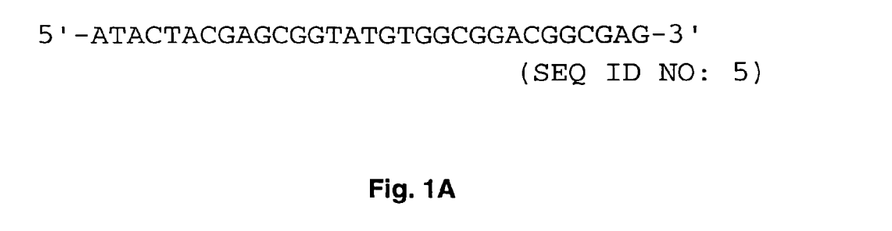
FIGS. 1A–1D are antisense sequences of part of the hMLH1 gene promoter.
Figure 1B:
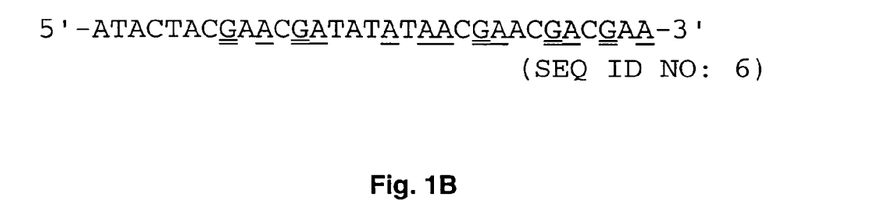
Figure 1C:
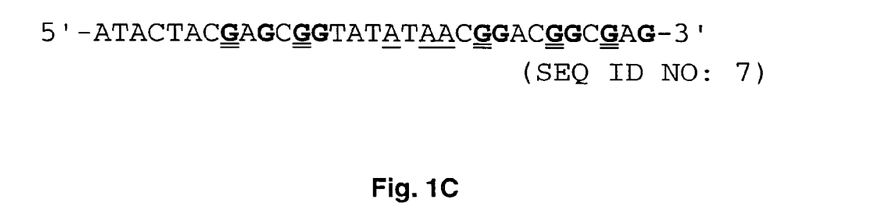
Figure 1D:
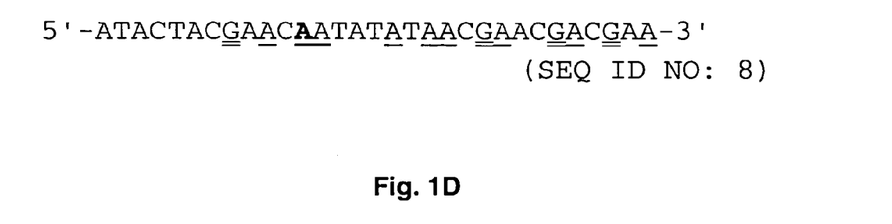

FIG. 1D is a sequence derived from the same DNA sample as that for FIG. 1C but after CpG retrieval. Here, all non-CpG cytosines are successfully converted to thymines (single-underlined A). Most CpG cytosines are methylated, which are viewed as G (double-underlined) in an antisense sequence except for one (A, bolded and single-underlined) which is free of methylation and thus is successfully converted.

EXAMPLE 3

Effects of Formalin Fixation on Sodium Bisulfite-Mediated DNA Modification for Methylation-Specific PCR Four xenografts were harvested and fixed in 10% formalin for 4, 8 and 24 hours before being processed and embedded in paraffin. Four DNA samples were collected from each xenograft: one from fresh tissue and three from tissues fixed in formalin for 4, 8 and 24 hours. The number of DNA samples was 16 for 4 xenografts.

All 16 samples were subjected to bisulfite modification with and without CpG retrieval (boiling in citrate buffer for 30 minutes). A total of 32 bisulfite-modified DNA samples were obtained.

All 32 samples were subjected to PCR amplification using both methylated-specific and unmethylated-specific primers for MGMT and MLH1 promoters. A total of 128 PCR reactions were performed.

All 128 PCR products were subcloned and 5 colonies for each sample were amplified for DNA sequencing. Efficiency of sodium bisulfite-mediated DNA modification between fresh and formalin-fixed xenograft tumor tissues were compared.

TABLE 3

| Xenografts | MGMT | MLH1 |
|---|---|---|
| Rh18 | ++ | − |
| HC1 | − | − |
| NB1382 | +/− | ++ |
| Rh66 | ++ | + |

Rh = rhabdomyosarcoma;
HC = colon carcinoma;
NB = neuroblastoma

EXAMPLE 4

Ataxia-telangiectasia-mutated (ATM) Promoter Methylation Status in Head and Neck Squamous Cell Carcinoma One hundred consecutive untreated cases of head and neck squamous cell carcinoma (HNSCC) were collected from the Anatomical Pathology file (from 1993 to 1998) cataloged by the Department of Pathology, John L. McClellan Memorial Veterans' Hospital, Little Rock, Ark. Both paraffin blocks and H&E-stained slides of tumors from each case were available for study. Case selection was based on the following criteria: primary surgical resection with curative intent or diagnostic biopsy for the purpose of adjuvant therapy, and no prior history of head and neck squamous cell carcinoma and adjuvant therapy. The histology of each case was reviewed and representative tissue blocks containing invasive SCC were selected for DNA extraction and promoter methylation analysis.

Clinical follow-up was available for all of the cases up to May, 2002. Pertinent patient information was retrieved from the Computerized Patient Record System, Department of Veterans Affairs. The patient population consisted of all males ranging in age from 45 to 85 years (mean, 65.8 years). The mean follow-up period for all of the patients was 51.2 months. Median survival based on all causes of death was 49.2 months. Of 31 surviving patients, the mean survival was 67.2 months (range, 8.4–144 months). Of the 47 patients with local recurrence or a second primary tumor, 43 (92%) died and 41 of these patients died of their cancer. Nine patients had more than one recurrence, and all died of their disease. Of the 53 patients without local recurrence or a second primary tumor, 26 (49%) died and 8 died of their disease. History of tobacco and alcohol use were recorded for some patients.

As a control, Ataxia-telangiectasia-mutated (ATM) promoter methylation status was analyzed in nonneoplastic tissue obtained from tonsillectomy procedures conducted on patients less than 70 years old. Noncancerous tissue was harvested from paraffin-embedded tissue sections using a Pixcell II LCM microscope (Arcturus Engineering, Mountain View, Calif.). DNA was subsequently extracted and analyzed as outlined below.

Genomic DNA harvested from head and neck squamous cell carcinoma and tonsillectomy specimens, as well as negative and positive control DNA samples, were subjected to bisulfite modification before methylation-specific PCR (MSP) using CpGenome DNA modification kit (Intergen).

Figure 2A:
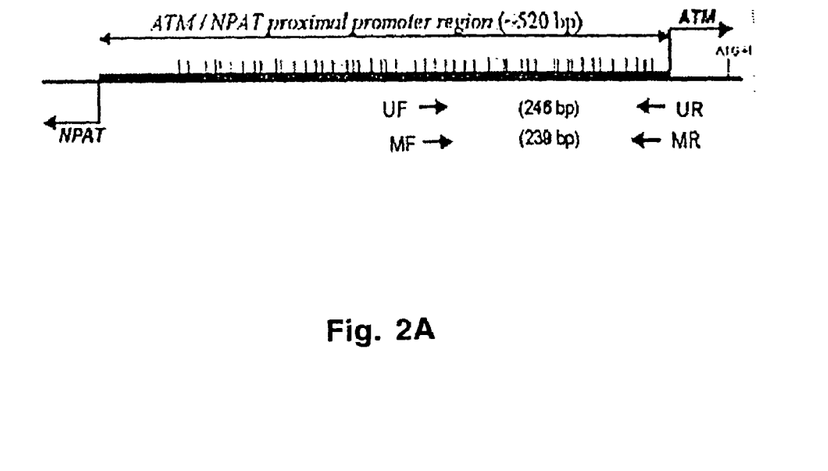

MSP analysis of the ATM promoter region was carried out in 25-ml PCR reactions containing 1 ml of bisulfite-treated genomic DNA, dNTPs (200 mM each), oligonucleotide primers (25 pmol each/reaction), 2.5 mM $MgCl_2$, and 0.625 units of Hotstar Taq (Qiagen, Valencia, Calif.) in 1×PCR buffer. Methylation-specific PCR primers for analysis of ATM gene promoter are: 5'-GTTTTGGAGTTTGAGT-TGAAGGGT-3' (sense) (SEQ ID NO:25) and 5'-AACTAC-CTACTCCCACTTCCAA-3' (antisense) (SEQ ID NO:26) for amplification of the promoter existing in an unmethylated state, and 5'-GGAGTTCGAGTCGAAGGGC-3' (sense) (SEQ ID NO:27) and 5'-CTACCTACTCCCGCT-TCCGA-3' (antisense) (SEQ ID NO:28) for amplification of the promoter existing in a methylated state. The primers were designed to amplify unmethylated ATM promoter sequence to yield an amplicon from nt −404 to −159, and the methylated primer set would yield an amplicon from nt −399 to −161 (numbering system based on location of the ATM translational start site). Thus, the predicted size of the unmethylated amplicon is 246 bp, and the methylated amplicon is 239 bp. A schematic diagram of the ATM proximal promoter region with the location of the ATM MSP primer sets is shown in FIG. 2A.

Thermocycling conditions used were: initial denaturation and hot start at 95° C. for 15 min; 40 cycles consisting of 30 s at 95° C., 30 s at 56° C. (unmethylated reactions), or 59° C. (methylated reactions), and 1 min at 72° C. After thermocycling, reactions were subjected to a 5-min, 72° C.

incubation. Positive and negative control reactions were run in parallel with each set of MSP reactions. MSP reactions were analyzed by electrophoresis on 2% agarose gels and were visualized by ethidium bromide staining.

Figure 2B:
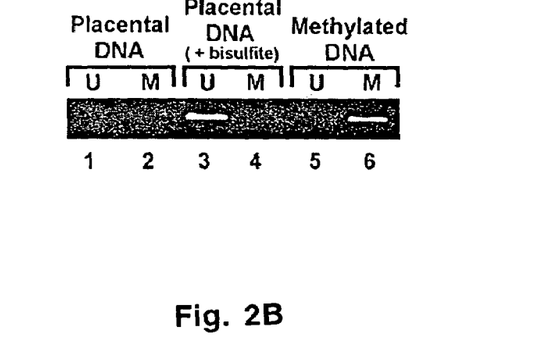
FIG. 2B shows non-bisulfite-modified human placental DNA (Lanes 1 and 2), bisulfite-modified placental DNA (Lanes 3,4), or bisulfite-modified universal methylated human genomic DNA (Lanes 5 and 6) was used in PCR reactions with unmethylated-specific (U) or methylated-specific (M) MSP primer sets.

To initially verify our designed primers, we tested these oligonucleotides in PCR reactions using human placental and methylated human DNA (FIG. 2B). It was observed that PCR reactions conducted on this non-bisulfite-modified DNA failed to result in accumulation of either unmethylated (U) or methylated (M) amplicon (FIG. 2B, lanes 1 and 2). This result indicates that productive amplification using either primer set requires bisulfite-modified template DNA. Next, bisulfite-modified placental DNA was tested and accumulation of only a 246-bp amplicon in reactions using unmethylated amplicon-specific primers (FIG. 2B, lane 3 and 4) was observed. PCR conducted on bisulfite-modified methylated human DNA showed only accumulation of the 239 methylated amplicon (FIG. 2B, lanes 5 and 6). The identity of these amplicons was confirmed by DNA sequencing.

Figure 2C:
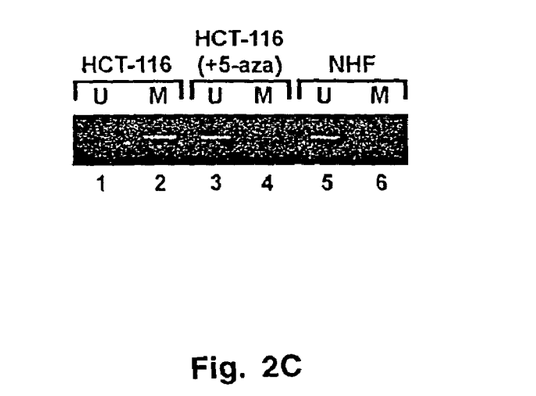
FIG. 2C shows bisulfite-modified genomic DNA harvested from HCT-116 cells (Lanes 1 and 2), HCT-116 cultured in the presence of 5-azacytidine (5-aza; Lanes 3 and 4), or normal human fibroblasts (Lanes 5 and 6) was used in PCR reactions with unmethylated (U) or methylated-specific (M) primer sets.

As a further verification step, this methylation-specific PCR (MSP) primer set was tested using genomic DNA harvested from the colorectal tumor line HCT-116. It was previously demonstrated, using a restriction enzyme-based approach, that this line displays aberrant methylation of the ATM proximal promoter region and that this correlated with markedly decreased ATM protein abundance. Consistent with previous findings, analysis of bisulfite-modified HCT-116 DNA with a MSP primer set showed accumulation of methylated-specific amplicon (FIG. 2C, lanes 1 and 2). Furthermore, MSP conducted on genomic DNA isolated from HCT-116 cells cultured in the presence of global demethylating agent 5-azacytidine (FIG. 2C, lanes 3 and 4) as well as genomic DNA from normal human foreskin fibroblasts (FIG. 2C, lanes 5 and 6) showed accumulation of unmethylated amplicon, consistent with the unmethylated nature of the ATM promoter in these cells. Taken together, these verification experiments indicate that these MSP primers amplify genomic DNA in a manner that clearly ascertain the methylation status of the ATM promoter.

Figure 3A:
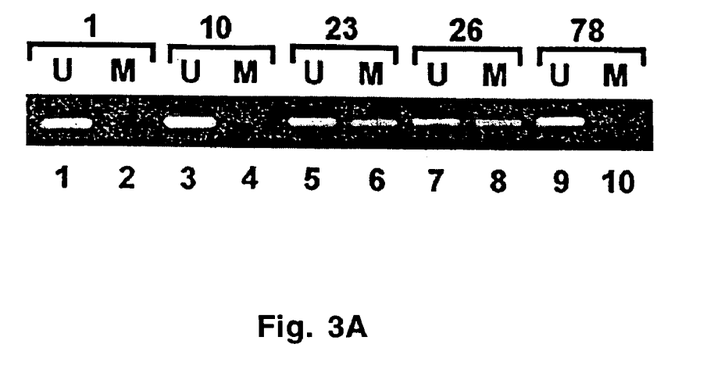
FIGS. 3A–C shows the ATM promoter is aberrantly methylated in head and neck squamous cell carcinoma (HNSCC).

These MSP primers were subsequently used to analyze genomic DNA extracted from fixed HNSCC tumors embedded in paraffin. To date, 100 consecutive untreated cases of HNSCC selected on the basis of criteria outlined above has been analyzed. FIG. 3A displays representative MSP data obtained from five head and neck squamous cell carcinoma samples. In tumor samples 1, 10, and 78, amplification was observed with the unmethylated-specific primers indicating a lack of ATM promoter hypermethylation in these tumor samples. Tumor samples 23 and 26 show amplification of both unmethylated and methylated-specific amplicons. Amplification of both unmethylated and methylated-specific MSP products is a common finding during analysis of tumor samples and could be attributable to contamination of tumor sample with normal cells. Alternatively, these results could stem from methylation of a single ATM allele within individual tumor cells, heterogeneous ATM promoter methylation within the tumor cell population, or both.

The 239-bp fragment amplified with the methylated-specific primer set contains a total of 25 CpG dinucleotides. To resolve the density of CpG methylation within the ATM promoter, methylation-specific amplicons from head and neck squamous cell carcinoma DNA were cloned and sequenced.

Figure 3B:
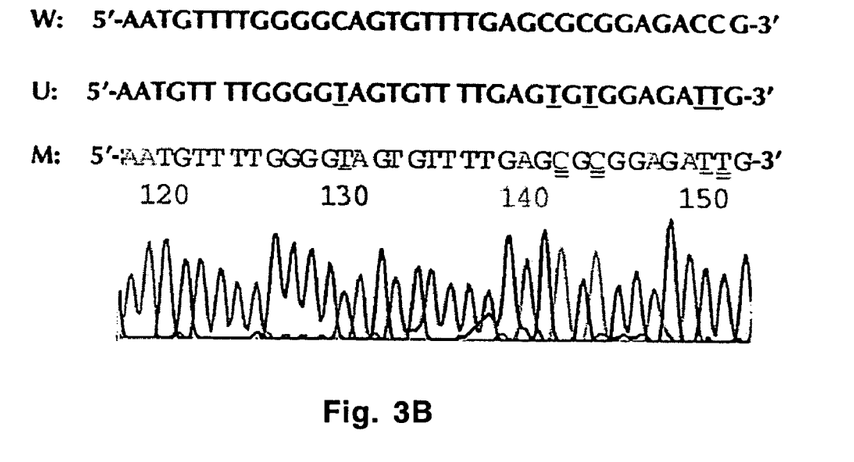

A representative DNA sequence chromatogram derived from a cloned, methylated-specific amplicon is shown in FIG. 3B. In this clone, sequencing revealed that two of the three CpG dinucleotides within the 35-bp region of the ATM promoter displayed are methylated. Moreover, sequencing of 17 cloned methylated-specific MSP amplicons derived from seven head and neck squamous cell carcinoma tumors revealed that >80% of the CpGs within this region of the ATM promoter are methylated in these tumors. Taken together, these findings indicate that a subset of head and neck squamous cell carcinoma tumors display dense methylation of the ATM promoter.

Figure 3C:
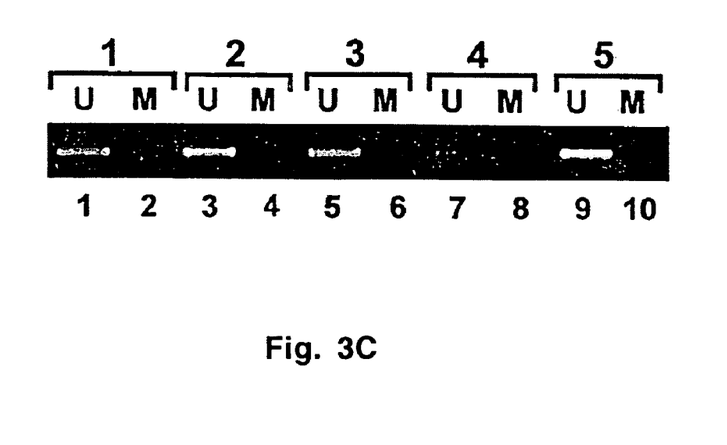

To examine ATM promoter hypermethylation in normal oral epithelium, eight noncancerous tonsillectomy tissues were analyzed by MSP. The results from five tonsillectomy specimens are shown (FIG. 3C), and no indication of ATM promoter methylation in these, or the other three tissues analyzed, was observed.

EXAMPLE 5

Ataxia-telangiectasia-mutated (ATM) Promoter Hypermethylation as a Prognostic Marker for Head and Neck Squamous Cell Carcinoma Methylation specific PCR (MSP) data collected on 100 head and neck squamous cell carcinoma tumors indicated that the ATM promoter was hypermethylated in 25 (25%) of these tumors. Association of ATM promoter hypermethylation with various clinical, pathological, and treatment parameters was analyzed using a cross-table $\chi^2$ test (Table 3). Of note, a statistically significant correlation was found between ATM promoter hypermethylation in primary head and neck squamous cell carcinoma tumors and initial diagnosis at age 65 or younger (P=0.05). However, no significant correlation was noted with other parameters such as tumor site and size, lymph node status, clinical stage, history of tobacco or alcohol use, and chemoradiation therapy.

Figure 4A:
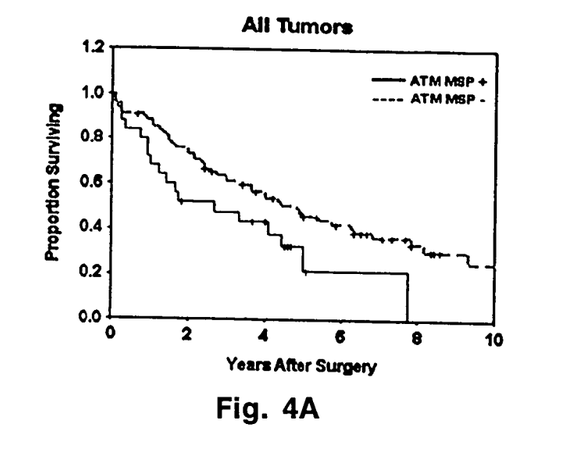
FIGS. 4A–C shows overall survival of 100 head and neck squamous cell carcinoma (HNSCC) patients as determined by the Kaplan-Meier method.

Applying a Kaplan-Meier survival test on the entire patient population, we found that ATM promoter hypermethylation was significantly correlated with decreased overall patient survival (P=0.03; Table 4; FIG. 4A) but not with disease-free survival (P=0.76). The overall 5-year survival is 22% in tumors with ATM promoter hypermethylation and 46% in those without ATM promoter hypermethylation (Table 4). Disease-free survival was defined as the time from tumor resection until the first evidence of tumor recurrence or the development of secondary primary tumor. Overall patient survival was defined as the time from tumor resection to the time of death due to all causes.

Multivariate analysis was also performed on this data set using the Cox regression model. This test indicated that ATM promoter hypermethylation could predict decreased overall patient survival, independent of other potential prognostic factors, such as tumor size, nodal status, clinical stage, and history of tobacco and alcohol use (P=0.03). ATM promoter hypermethylation may also correlate with decreased cause-specific survival but this correlation did not reach statistical significance (P=0.09).

Figure 4B:
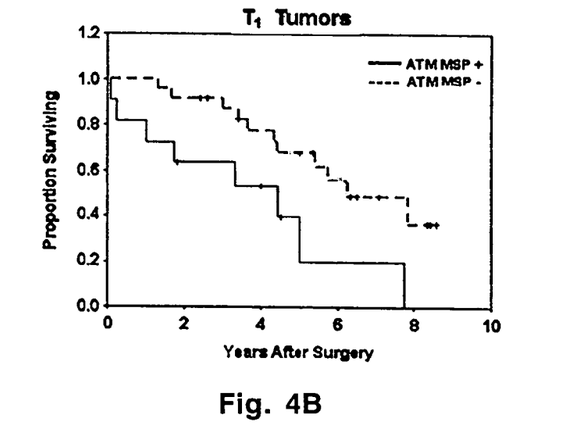
Figure 4C:
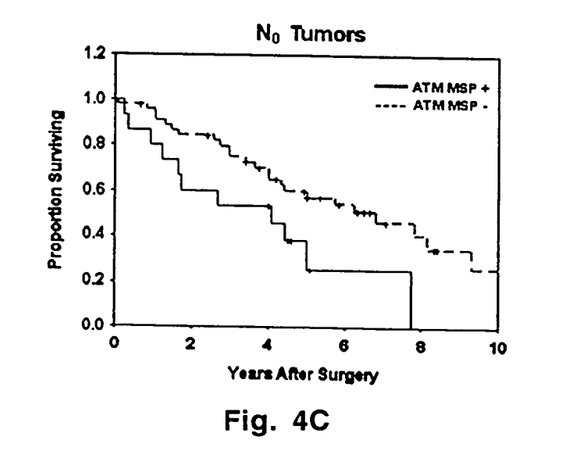

Finally, association of ATM promoter hypermethylation with overall patient survival was further stratified by tumor size (T stage) and lymph node status (N stage; Table 4). ATM promoter hypermethylation was found to be significantly correlated with decreased overall survival in tumors of small size (T1; P=0.01; Table 4; FIG. 4B) and tumors without lymph node spread ($N_0$; P=0.03; Table 4; FIG. 4C). No significant statistical correlation was observed between ATM promoter hypermethylation and overall survival rate in larger tumors (T2, T3, or T4; P=0.29), or tumors with nodal metastasis ($N_1$, $N_2$; P=0.38; Table 4).

As stated above, the proportion of head and neck squamous cell carcinoma patients surviving 5 years post-diagnosis is 46% when the ATM promoter is not methylated compared with 22% when the ATM promoter is methylated. Again, when these data were stratified by tumor size and nodal status, a significant correlation persists in $T_1$ and $N_0$ tumors. The overall 5-year survival rate is 68% ($T_1$ tumor) and 57% ($N_0$ tumor) when the ATM promoter is not methylated, and 20% ($T_1$ tumor) and 25% ($N_0$ tumor) when the ATM promoter is methylated. Each of these criteria was found to be statistically significant. Taken together, these data suggest that ATM promoter methylation has a more prominent impact on patient survival in early-stage tumor development.

In summary, using a stringently verified set of methylation-specific PCR primers, we documented that the ATM promoter is a target for aberrant hypermethylation in head and neck squamous cell carcinoma. Given the important role that ATM plays in the maintenance of genome integrity and the causative role that genome instability plays in cancer onset and progression, reduced ATM function through epigenetic silencing is an attractive candidate mechanism contributing to head and neck squamous cell carcinoma and, perhaps, other tumor types. These results also indicate that ATM promoter methylation may be a useful prognostic marker in head and neck squamous cell carcinoma.

The following references were cited herein:

Herman et al., *Proc Natl Acad Sci USA*. 93:9821–9826 (1996)
Fleisher et al., *Cancer Res.* 59:1090–1095 (1999).
Fleisher et al., *Cancer Res.* 60:4864–4868 (2000).
Frommer et al., *Proc. Natl. Acad Sci. USA* 89:1827–1831 (1992).
Sadri and Hornsby, *Nucl. Acids Res.* 24:5058–5059 (1996).
Xiong and Laird, *Nucl. Acids Res.* 25:2532–2534 (1997).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

TABLE 4

Association of Various Potential Prognostic Factors With Ataxia-telangiectasia mutated (ATM) Methylation-Specific PCR (MSP) Results In Head And Neck Squamous Cell Carcinoma Patients

| Prognostic factors | No. of patients | ATM MSP + | % | $\chi^2$ P[a] |
|---|---|---|---|---|
| All patients | 100 | 25 | 25.0 | |
| Age | | | | |
| <65 yr | 47 | 16 | 34.0 | 0.05 |
| ≧65 yr | 53 | 9 | 17.8 | |
| Tumor site | | | | |
| Lip | 19 | 3 | 15.8 | 0.37 |
| Oral cavity | 42 | 14 | 33.3 | |
| Pharynx | 16 | 4 | 25.0 | |
| Larynx | 23 | 4 | 17.4 | |
| Tumor stage (T)[b] | | | | |
| 1 | 35 | 11 | 31.4 | 0.55 |
| 2 | 21 | 6 | 28.6 | |
| 3 | 19 | 3 | 15.8 | |
| 4 | 25 | 5 | 25.0 | |
| Lymph node stage (N)[b] | | | | |
| 0 | 60 | 15 | 25.0 | 1.00 |
| ≧1 | 40 | 10 | 25.0 | |
| Clinical stage[c] | | | | |
| I | 28 | 7 | 25.0 | 0.87 |
| II | 13 | 3 | 23.1 | |
| III | 15 | 5 | 33.3 | |
| IV | 44 | 10 | 22.7 | |
| Tobacco[d] | | | | |
| No | 12 | 4 | 33.3 | 0.42 |
| Yes | 54 | 12 | 22.2 | |
| Alcohol[d] | | | | |
| No | 20 | 5 | 25.0 | 0.96 |
| Yes | 47 | 12 | 25.0 | |
| Radiation therapy[d] | | | | |
| No | 41 | 10 | 24.4 | 0.86 |
| Yes | 46 | 12 | 26.1 | |
| Chemotherapy[d] | | | | |
| No | 60 | 14 | 23.3 | 0.65 |
| Yes | 25 | 7 | 28.0 | |

[a] Ps were obtained after correction for multiple comparisons within each prognostic group.
[b] Stage was determined by pathological examination.
[c] Clinical stage was determined by combining T, N, and M (distant metastasis) stage.
[d] The total number for tobacco, alcohol use, radiation or chemotherapy was less than 100 cases because some of these data were not available in patients' files, and, thus were excluded for statistical analysis.

TABLE 5

Association of Ataxia-telangiectasia-mutated (ATM) Promoter Methylation With Overall Survival Among Different Patient Subpopulations

| ATM MSP[a] results | No. of patients at risk | No. of deaths | Probability of surviving 5 yr[b] | Hazard ratio | Log-rank P[c] | Adjusted P[c] |
|---|---|---|---|---|---|---|
| All tumors | | | | | | |
| − | 75 | 51 | 0.46 | 1.44 | 0.03 | |
| + | 25 | 18 | 0.22 | | | |
| $T_1$[d] | | | | | | |
| − | 24 | 11 | 0.68 | 2.50 | 0.01 | 0.02 |
| + | 11 | 8 | 0.20 | | | |
| $T_{2-4}$ | | | | | | |
| − | 51 | 40 | 0.35 | 1.12 | 0.29 | |
| + | 14 | 10 | 0.27 | | | |
| $N_o$[d] | | | | | | |
| − | 45 | 26 | 0.57 | 1.74 | 0.03 | 0.03 |
| + | 15 | 11 | 0.25 | | | |
| $N_{1-2}$ | | | | | | |
| − | 30 | 25 | 0.29 | 1.03 | 0.38 | |
| + | 10 | 7 | 0.27 | | | |

[a] MSP, methylation-specific PCR; T, tumor; N, lymph node.
[b] All survival data were presented as cumulative probability.
[c] Log-rank test is a test of equality of survivor function across groups; adjusted Ps for multiple log-rank tests were obtained using a Wilcoxon (Gehan) method.
[d] Stage was determined by pathological examination.

What is claimed is:

1. A method of predicting overall patient survival for patient with head and neck squamous cell carcinoma, comprising the steps of:
   obtaining tissue samples from the patient;
   extracting genomic DNA from the tissue samples; and
   determining promoter methylation status of ataxia-telangiectasia-mutated (ATM) gene, wherein hypermethylation of the ATM gene promoter indicates the patient would have decreased overall survival.

2. The method of claim 1, wherein the promoter methylation status is determined by methylation-specific PCR.

3. The method of claim 2, wherein the methylation-specific PCR utilizes primers selected from the group consisting of SEQ ID NOs: 25–28.

* * * * *